United States Patent [19]

Burton

[11] Patent Number: 4,739,000
[45] Date of Patent: Apr. 19, 1988

[54] ANTIOXIDANT AROMATIC TETRAPHOSPHITES

[75] Inventor: Lester P. J. Burton, Baton Rouge, La.

[73] Assignee: Ethyl Corporation, Richmond, Va.

[21] Appl. No.: 888,159

[22] Filed: Jul. 22, 1986

[51] Int. Cl.$^4$ .................. C08K 5/52; C07F 9/145
[52] U.S. Cl. ........................... 524/128; 558/156
[58] Field of Search ..................... 558/156; 524/128

[56] References Cited

U.S. PATENT DOCUMENTS

| | | | |
|---|---|---|---|
| 2,847,443 | 8/1958 | Hechenbleikner et al. | 558/156 |
| 3,281,381 | 10/1966 | Hechenbleikner et al. | 558/156 |
| 4,341,721 | 7/1982 | Batorewicz | 558/156 |

Primary Examiner—Anton H. Sutto
Attorney, Agent, or Firm—J. F. Sieberth; J. D. Odenweller

[57] ABSTRACT

An aromatic tetraphosphite suitable for use as an antioxidant for organic materials. The aromatic tetraphosphite has the formula:

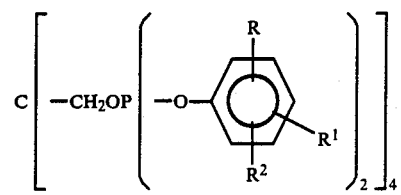

wherein R, R$^1$ and R$^2$ are independently selected from the group consisting of hydrogen and straight chain, branched and cyclic alkyl groups having from 1 to about 18 carbon atoms with the provision that at least two of the R, R$^1$ and R$^2$ groups are alkyl groups.

8 Claims, No Drawings

ANTIOXIDANT AROMATIC TETRAPHOSPHITES

BACKGROUND OF THE INVENTION

1. Field of the Invention

This invention relates to hydrolytically stable aromatic tetraphosphites and their use as antioxidants in organic materials such as organic polymers.

2. Description of the Prior Art

Phosphites are used in organic polymers and other organic materials as antioxidants. The phosphites are generally considered better than phenolic antioxidants at high temperatures because they eliminate hydroperoxides which decompose and lead to autooxidation chain reactions. Thus, phosphites are important for oxidative stability during various operations including polyolefin extrusion.

Phenolic and phosphite antioxidants are often used together in polyolefin homopolymers and copolymers to provide antioxidant protection for both low and high temperature exposure. Unfortunately, additional expense is encountered as additives in larger amounts are needed for the polymers. Thus, there exists a need for effective antioxidants at a reasonable additive price, not only for polyolefins, but other substrates as well.

It is common practice to include an antioxidant in organic materials normally susceptible to oxidative degradation. Many of the antioxidants employed have limited effectiveness or tend to impart undesirable properties to the organic material such as causing color. The problem is particularly acute with polymers and copolymers of ethylenically unsaturated monomers, especially polyolefins such as polyethylene or polypropylene. These materials are subjected to elevated temperatures during processing, which tends to destroy many antioxidants with the result that the polymer rapidly degenerates during use. The compounds of the present invention allow organic materials to maintain excellent color and thermal stability.

SUMMARY OF THE INVENTION

According to the present invention, certain pentaerythritol octaaryl tetraphosphites are provided which are very effective as stabilizers in a wide range of organic materials.

The pentaerythritol octaaryl tetraphosphites are very effective antioxidants because they retard changes in viscosity of organic materials stabilized therewith for extensive periods of time under oxidative conditions. In addition, they are stable when stored at room temperatures. The phosphites of the invention are especially effective when used in combination with phenolic antioxidants.

DESCRIPTION OF THE PREFERRED EMBODIMENTS

The pentaerythritol octaaryl tetraphosphites of the present invention are particularly useful as an antioxidant for an organic material normally susceptible to degradation in the presence of oxygen by including in the organic material an antioxidant amount of the pentaerythritol octaaryl tetraphosphites.

The pentaerythritol octaaryl tetraphosphites of the present invention are represented by the formula:

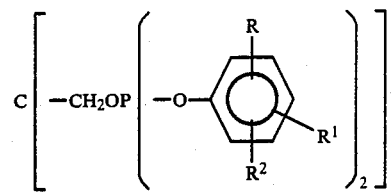

wherein R, $R^1$ and $R^2$ are each independently selected from the group consisting of hydrogen and straight chain, branched and cyclic alkyl groups having from 1 to about 18 carbon atoms with the provision that at least two of the R, $R^1$ and $R^2$ groups are alkyl groups.

Examples of R, $R^1$ and $R^2$ include hydrogen and alkyl groups such as methyl, ethyl, propyl, isopropyl, butyl, sec-butyl, isobutyl, tert-butyl, pentyl, isopentyl, isohexyl, 3-methylpentyl, 2,3-dimethylbutyl, heptyl, octyl, nonyl, decyl, undecyl, dodecyl, tetradecyl, hexadecyl, octadecyl, cyclopentyl, cyclohexyl and the like.

Preferably, R, $R^1$ and $R^2$ are tertiary alkyl groups containing 4 to about 18 carbon atoms such as tertiary butyl, tertiary pentyl, tertiary hexyl, tertiary heptyl, tertiary octyl, tertiary nonyl, tertiary decyl and the like. More preferably R and $R^1$ are tertiary butyl, $R^2$ is hydrogen and R is located in an ortho position of each phenyl moiety and $R^1$ is located in the para position of each phenyl moiety.

The preferred phosphite of the present invention is pentaerythritol octakis(2,4-di-tert-butylphenyl)tetraphosphite which is represented by the formula:

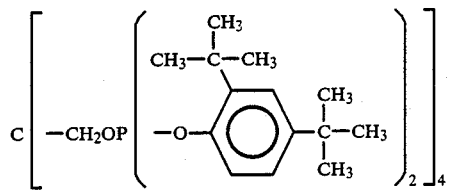

The phosphites of the invention are particularly useful as antioxidants. The antioxidants can be used in a broad range of organic material normally subject to gradual degradation in the presence of oxygen during use over an extended period. In other words, the organic materials protected by the present antioxidants are of the type in which the art recognizes the need for antioxidant protection and to which an antioxidant of some type is customarily added to obtain an extended service life. The oxidative degradation protected against is the slow gradual deterioration of the organic composition rather than, for example, combustion.

Examples of organic materials in which the antioxidants are useful include polymers, both homopolymers and copolymers, of olefinically unsaturated monomers, for example, polyolefins such as polyethylene, polypropylene, polybutylene, and the like.

Also, polyhalohydrocarbons such as polyvinyl chloride, polychloroprene, polyvinylidene chloride, polyfluoroolefins, and the like, are afforded stabilization. The antioxidants provide antioxidant protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylene-vinyl acetate copolymers are protected, as are butene-methylacrylate copolymers. Nitrogen-containing polymers such as polyurethanes, nitrile rubber, and lauryl acrylate-vinyl pyrrolidone copolymers are effectively stabilized. Adhesive compositions such as solutions of polychloroprene (neoprene) in toluene are protected.

Petroleum oils such as solvent-refined, midcontinent lubricating oil and Gulf Coast lubricating oils are effectively stabilized. In hydrocarbon lubricating oils, both mineral and synthetic, the present antioxidants are particularly effective when used in combination with a zinc dihydrocarbyl dithiophosphate e.g. zinc dialkyl dithiophosphate or zinc dialkaryl dithiophosphate.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethylene glycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1-6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The antioxidants of the present invention are preferably used in either thermoset or thermoplastic polymer compositions. The thermoset polymers are those plastics which when subjected to heat, will normally become infusible or insoluble and as such cannot be remelted. They have elaborately cross-linked three dimensional structures and are used for plastics, elastomers, coatings and adhesives.

In contrast to the thermoset polymers, most thermoplastic polymers can be made to soften and take a new shape by the application of heat and pressure. Thermoplastic polymers comprise long-chain molecules often without any branching (e.g., high density polyethylene). Thermoplastic polymers normally are rigid at operating temperatures, but can be remelted and reprocessed. They include polyethylene, polycarbonate, polypropylene, polystyrene, polyvinyl chloride, acrylonitrile-butadiene-styrene (ABS), nylon, and the like, including polymers intended for high temperature applications. The most preferred organic compounds intended for the practice of the present invention are polypropylene and polyethylene.

The antioxidants are incorporated into the organic material in a small but effective amount so as to provide the required antioxidant protection. A useful range is generally from about 0.005 to about 5 weight percent of organic material, and a preferred range is from about 0.01 to 2 weight percent.

Methods of incorporating the antioxidants into the organic material are well known. For example, if the material is liquid, the additive can be merely mixed into the material. Solid organic materials can be merely sprayed with a solution of the additive in a volatile solvent. For example, stabilized grain products result from spraying the grain with a toluene solution of the antioxidant. In the case of rubbery polymers, the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The phosphites of the present invention can be prepared by reacting an alkylated phenol and a phosphorus trihalide such as $PCl_3$ or $PBr_3$ in the presence of a solvent to form an intermediate diaryl halophosphite and subsequently reacting the intermediate product with pentaerythritol to produce the phosphites. The intermediate diaryl halophosphite may be isolated and purified prior to its reaction with pentaerythritol or may be reacted with the pentaerythritol in a one reactor, sequential process.

Alkylated phenols suitably used in preparing the phosphites of the present invention have the formula:

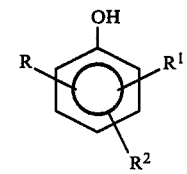

wherein R, $R^1$ and $R^2$ are all as previously defined.

The reaction of the alkylated phenol and the phosphorus trihalide is carried out at a temperature sufficient to cause the reaction to proceed to mainly diarylphosphite formation, but not so high as to cause excessive triarylphosphite formation or reactant or product decomposition. Thus, generally the temperature used in the preparation of the intermediate product is in the range of from about $-10°$ C. to about $300°$ C. The preferred temperature range is from about $5°$ C. to about $100°$ C.

The reaction of the intermediate diaryl halophosphite and pentaerythritol is carried out at a temperature sufficient to produce the phosphites of the present invention, but not so high as to cause the production of undesirable byproducts or reactant or product decomposition. Thus, generally, the temperature used in the preparation of the phosphites is in the range of from about −10° C. and preferably from about 5° C. to about 100° C.

Solvents used in the production of the phosphites of the present invention are aprotic solvents. Examples of such solvents include toluene, xylene, hexane, heptane, tetrahydrofuran, and diethyl ether. The preferred solvents are toluene and tetrahydrofuran.

The preferred reaction conditions include a pressure high enough to allow the reaction to proceed at a reasonable rate yet not so high as to adversely affect the course of the reaction. The preferred pressure range extends from atmospheric to about 1000 psig. No significant advantage is obtained by running the reaction under high pressures. Therefore, the reaction is generally run at atmospheric pressure.

No particular type of atmosphere is required. However, a nitrogen atmosphere is generally preferred since it is a common way of keeping oxygen and moisture out of the reaction system.

The octaaryl tetraphosphites of the present invention may be used alone as the antioxidant or may be used in combination with phenolic antioxidants, light stabilizers such as hindered amines or ultraviolet light absorbers, metal deactivators, pigments, dyes, lubricants such as calcium stearate, nucleation agents, and talc and other fillers.

Phenolic antioxidants which are suitable for use in the present invention are well known in the art and include 2,6-di-t-butyl-4-methylphenol, 2,6-di-t-butyl-4-methoxymethylphenol, 2,6-dioctadecyl-4-methylphenol, 3,5-di-t-butyl-4-hydroxyanisole, 2,5-di-t-butyl-4-hydroxyanisole, 4-(hydroxymethyl)-2,6-di-t-butylphenol, 4,4'-methylenebis(2,6-di-t-butylphenol), 2,2'-ethylidenebis(4,6-di-t-butylphenol), 4,4'-thiobis(2-methyl-6-t-butylphenol), tetrakis(methylene 3-(3,5-di-t-butyl-4-hydroxyphenyl)propionate)methane, 1,3,5-tris(3,5-di-t-butyl-4-hydroxybenzyl)isocyanurate, O,O'-di-n-octadecyl(3,5-di-t-butyl-4-hydroxybenzyl)phosphonate, octadecyl 3-(3,5-di-t-butyl-4-hydroxyphenyl)propionate, 2,2'-oxamidobisethyl 3-(3,5-di-t-butyl-4-hydroxyphenyl)propionate, calcium bis(O-ethyl(3,5-di-t-butyl-4-hydroxybenzyl)phosphonate) and mixtures thereof. A particularly preferred phenolic antioxidant is 1,3,5-trimethyl-2,4,6-tris(3,5-di-t-butyl-4-hydroxybenzyl)benzene which is available from Ethyl Corporation as Ethanox ®330 antioxidant.

When utilized, the phenolic antioxidants are preferably present with the aromatic diphosphites in an amount in the range of from about 0.005 to about 3.0 percent by weight based on the weight of the total composition.

The following examples are presented to illustrate certain specific embodiments of the invention, but are not intended to be construed so as to be restrictive of the spirit and scope thereof.

EXAMPLE 1

Preparation of Pentaerythritol Octakis(2,4-di-tert-butylphenyl)Tetraphosphite

Under a nitrogen atmosphere, 30 ml of $PCl_3$ and 500 ml of toluene were combined to form an admixture. A solution containing 141 grams of 2,4-di-t-butylphenol, 100 ml of triethylamine, and 100 ml of toluene was added dropwise to the admixture over a period of time of about 50 minutes. An exotherm was observed during the addition. The resulting slurry was filtered. The filtrate was concentrated to 253 grams of yellow oil. The oil was flash distilled to yield bis(2,4-di-t-butylphenyl)chlorophosphite.

Under a nitrogen atmosphere, an 11.0 gram portion of the bis(2,4-di-t-butylphenyl)chlorophosphite (85% purity), 3 ml of triethylamine and 50 ml of tetrahydrofuran were combined to form an admixture and warmed to 40° C. A 0.68 gram portion of pentaerythritol was added to the admixture. The resulting mixture was heated to 65° C. and maintained at this temperature for 2 hours. The resulting slurry was filtered. The filtrate was concentrated under vacuum to 14.5 grams of yellow oil. The oil was stirred in 75 ml of acetonitrile. The white solids, which were formed (8 grams), were collected. A 5.8 gram portion of the solids were chromatographed through 30 grams of Florisil (100–200 mesh), eluting with n-heptane to yield 4.0 grams of pentaerythritol octakis(2,4-di-tert-butylphenyl)tetraphosphite.

EXAMPLE 2

In order to demonstrate the effectiveness of the phosphites of the present invention as processing stabilizers, pentaerythritol octakis(2,4-di-tert-butylphenyl)tetraphosphite (hereinafter referred to as "Phos.A") and, 1,3,5-trimethyl-2,4,6-tris(3,5-di-t-butyl-4-hydroxybenzyl)benzene (Ethanox ®330 antioxidant) were incorporated into polypropylene powder in accordance with the following procedure. The Phos.A and Ethanox ®330 antioxidant were dissolved in a small amount of methylene chloride and mixed with 50 g of polypropylene powder (Profax 6501 from Hercules). The mixture was then dry blended with 450 g of polypropylene in a nitrogen atmosphere. In all formulations, 1000 ppm of calcium stearate (Mallinckrodt RSN 248D) was utilized as an acid neutralizer and lubricating agent. The blended material was extruded under nitrogen on a twin screw mixer (Brabender, 30 rpm) with the temperature profile: zone one—150° C., zone two and zone three—245° C. Then, multiple extrusions were run on the pellets on a single screw extruder (Brabender L/D 24:1) at 500° F. The stock temperature was 265° C. and the screw speed was 30 rpm in an air atmosphere. The extruded strand was cooled by passing it through a room temperature (24°–29° C.) water bath. Water carryover was minimized by an air knife that blew the excess water from the strand before it entered the pelletizer. Physical properties were measured after the initial and subsequent passes through the extruder to assess the progress of degradation. The melt flow index (MFI) was determined with a Tinium Olsen Extrusion Plastometer according to ASTM Method D-1238 Condition L (230° C.–2160 g load).

The results of these tests are shown in Table I.

TABLE I

| Test No. | Antioxidant | Wt. % | Melt Flow Index Extrusion Pass No. | | |
|---|---|---|---|---|---|
| | | | 1 | 3 | 5 |
| 1 | None | — | 5.0 | 13.9 | — |
| 2 | Ethanox 330 | 0.05 | 3.2 | 6.2 | 9.8 |
| 3 | Ethanox 330 Phos. A | 0.05 0.05 | 2.3 | 3.0 | 4.6 |

The results of these tests demonstrate that Phos.A was effective in reducing the degradation of polypropylene.

EXAMPLE 3

A series of tests were performed in the same manner as Example 2 except that a different batch of Profax 6501 polypropylene was used, no calcium stearate was added, and the extrusions were carried out at 550° F. In addition, using the same samples, a 60 ml sheet was pressed out at 375° C. and the color was determined with a Hunterlab Optical Sensor Model D25.

The results of these tests are shown in Table II.

TABLE II

| Test No. | Antioxidant | Wt. % | Melt Flow Index Extrusion Pass No. | | | Yellowness Index Extrusion Pass No. | | |
|---|---|---|---|---|---|---|---|---|
| | | | 1 | 2 | 3 | 1 | 2 | 3 |
| 1 | None | — | 9.3 | 19.2 | — | 6.5 | 8.5 | — |
| 2 | Ethanox 330 | 0.05 | 6.7 | 9.4 | 12.6 | 7.2 | — | 9.6 |
| 3 | Ethanox 330 Phos. A | 0.05 0.05 | 6.3 | 8.8 | 12.7 | 5.4 | — | 6.5 |

These results of these tests demonstrate that Phos.A was effective in reducing the degradation of polypropylene and suppressing the formation of color.

EXAMPLE 4

A series of tests were performed in the same manner as Example 3 except that calcium stearate was added to the test samples.

The results of these tests are shown in Table III.

TABLE III

| Test No. | Antioxidant | Wt. % | Melt Flow Index Extrusion Pass No. | | | Yellowness Index Extrusion Pass No. | | |
|---|---|---|---|---|---|---|---|---|
| | | | 1 | 2 | 3 | 1 | 2 | 3 |
| 1 | None | — | 13.8 | 26.9 | — | 5.0 | 6.2 | — |
| 2 | Ethanox 330 | 0.05 | 8.9 | 13.2 | 18.8 | 4.5 | — | 6.1 |
| 3 | Ethanox 330 Phos. A | 0.05 0.05 | 6.2 | 8.7 | 12.6 | 4.5 | — | 5.8 |

The results of these tests demonstrate that Phos.A was effective in reducing the degradation of polypropylene.

EXAMPLE 5

Tests were carried out by first dissolving or dispersing either 2,2'-ethylidenebis(4,6-di-t-butylphenol) (a phenolic antioxidant which is available from Ethyl Corporation as Ethanox ®308 antioxidant) or a mixture of Ethanox ®308 antioxidant and Phos.A in a small amount of methylene chloride. The admixture was mixed with 50 g of high density polyethylene (Soltex XF-397 which is available from Solvey et Cie). The resulting mixtures were then dry blended with 450 g of high density polyethylene under nitrogen. The blended materials were pelletized under nitrogen on a twin screw mixer (Brabender) with the following profile: zone one at 150° C., zones two and three at 200° C.; stock temperature at 204°-206° C.; screw speed 30 rpm. Then, multiple extrusions (5 passes) were run on the pellets on a single screw extruder (Brabender L/D 24:1) with a temperature profile of the following: zones one and two at 218° C., zone three at 232° C. and zone four at 246° C. The stock temperature was 253°-255° C. and the screw speed 30 rpm in an air atmosphere. The extruded strand was cooled by passing it through a room temperature (24°-29° C.) water bath. Water carryover was minimized by an air knife that blew the excess water from the strand before it entered the pelletizer. Material from each pass was collected and 60 mil sheets were pressed out at 375° F., and color was determined with a Hunterlab Optical Sensor Model D 25.

The results of these tests are shown in Table IV.

TABLE IV

| Test No. | Antioxidant | Wt % | Yellowness Index Extrusion Pass No. | | |
|---|---|---|---|---|---|
| | | | 1 | 3 | 5 |
| 1 | Ethanox 308 | 0.05 | 8.5 | 12.9 | 15.0 |
| 2 | Phos. A Ethanox 308 | 0.05 0.05 | 3.9 | 5.5 | 7.7 |
| 3 | Ethanox 308 Zinc Stearate | 0.10 0.05 | 1.6 | 3.8 | 6.9 |
| 4 | Ethanox 308 Phos. A Zinc Stearate | 0.10 0.05 0.05 | −0.34 | 1.9 | 4.7 |

The results of these tests show that Phos.A was effective in suppressing the formation of color.

The invention is not limited to the above-described specific embodiments thereof; it must be understood, therefore, that the detail involved in the descriptions of the specific embodiments is presented for the purpose of illustration only, and that reasonable variations, which will be apparent to those skilled in the art, can be made in this invention without departing from the spirit and scope thereof.

I claim:

1. A hydrolytically stable phosphite stabilizer namely pentaerythritol octakis(2,4-di-tert-butylphenyl)tetraphosphite.

2. A polyolefin composition containing a stabilizing amount of the phosphite of claim 1.

3. A composition of claim 2 containing an antioxidant amount of 1,3,5-trimethyl-2,4,6-tris(3,5-di-tert-butyl-4-hydroxybenzyl)benzene.

4. A composition of claim 3 containing calcium stearate.

5. A composition of claim 3 wherein said polyolefin is polypropylene.

6. A composition of claim 2 containing an antioxidant amount of 2,2'-ethylidenebis(4,6-di-tert-butylphenol).

7. A composition of claim 6 containing zinc stearate.

8. A composition of claim 6 wherein said polyolefin is polypropylene.

* * * * *

UNITED STATES PATENT AND TRADEMARK OFFICE
CERTIFICATE OF CORRECTION

PATENT NO. : 4,739,000
DATED : APRIL 19, 1988
INVENTOR(S) : LESTER P. J. BURTON

It is certified that error appears in the above-identified patent and that said Letters Patent is hereby corrected as shown below:

Column 5, lines 5-6 read " $-10^{\circ}C$ and preferably" and should read -- $-10^{\circ}C$ to about $300^{\circ}C$ and preferably -- .

Signed and Sealed this

Twenty-fifth Day of October, 1988

Attest:

DONALD J. QUIGG

*Attesting Officer*  *Commissioner of Patents and Trademarks*